(12) United States Patent
Guala

(10) Patent No.: US 7,658,726 B2
(45) Date of Patent: Feb. 9, 2010

(54) DRIP CHAMBER WITH INTEGRATED FLOW REGULATOR FOR MEDICAL LINES

(75) Inventor: Gianni Guala, Turin (IT)

(73) Assignee: Industrie Borla S.p.A. (IT)

( * ) Notice: Subject to any disclaimer, the term of this patent is extended or adjusted under 35 U.S.C. 154(b) by 342 days.

(21) Appl. No.: 11/492,652

(22) Filed: Jul. 25, 2006

(65) Prior Publication Data

US 2007/0043325 A1   Feb. 22, 2007

(30) Foreign Application Priority Data

Jul. 25, 2005   (IT) .......................... TO20050106 U

(51) Int. Cl.
*A61M 5/14*   (2006.01)
(52) U.S. Cl. .................................... 604/252
(58) Field of Classification Search ................ 604/251, 604/252, 246, 247, 248; 251/149
See application file for complete search history.

(56) References Cited

U.S. PATENT DOCUMENTS

| 4,317,473 A | 3/1982 | Gaydos ....................... 138/45 |
|---|---|---|
| 4,343,305 A | 8/1982 | Bron ....................... 128/214 R |
| 4,396,016 A * | 8/1983 | Becker ....................... 604/126 |
| 4,869,457 A * | 9/1989 | Ewerlof ......................... 251/6 |
| 5,098,407 A * | 3/1992 | Okamura ................... 604/248 |
| 5,098,408 A | 3/1992 | Tarzian ....................... 604/248 |
| 5,360,412 A * | 11/1994 | Nako et al. ................ 604/247 |
| 6,261,267 B1 | 7/2001 | Chen ......................... 604/247 |
| 6,619,308 B2 * | 9/2003 | Massengale et al. .......... 137/12 |
| 7,327,273 B2 * | 2/2008 | Hung et al. ................. 340/619 |
| 2007/0018129 A1 * | 1/2007 | Guala ......................... 251/149 |

FOREIGN PATENT DOCUMENTS

| DE | 202 16 791 U1 | 2/2003 |
|---|---|---|
| EP | 1 312 388 A1 | 5/2003 |
| WO | WO 03/047660 A1 | 6/2003 |

OTHER PUBLICATIONS

European Search Report for EP 06117317.5-2310, dated Oct. 13, 2006.

* cited by examiner

*Primary Examiner*—Nicholas D Lucchesi
*Assistant Examiner*—Aarti B Berdichevsky
(74) *Attorney, Agent, or Firm*—Heslin Rothenberg Farley & Mesiti P.C.; Victor A. Cardona

(57) ABSTRACT

Described herein is a drip chamber for medical lines with a generally cylindrical body having an inlet, on which a precision flow regulator is directly applied.

4 Claims, 3 Drawing Sheets

DRIP CHAMBER WITH INTEGRATED FLOW REGULATOR FOR MEDICAL LINES

CROSS REFERENCE TO RELATED APPLICATIONS

This application is a claims priority from Italian Utility Model Application No. TO2005A000106 filed on Jul. 25, 2005, the entire disclosure of which is incorporated herein by reference.

FIELD OF THE INVENTION

The present invention relates to drip chambers formed by a generally cylindrical body having an inlet and an outlet, traditionally used in medical lines, for example for infusion or transfusion, to supply, in a dosed way, a medical liquid, normally contained in a sac or bottle, to a patient.

In use, set between the sac or bottle of the medical liquid and the drip chamber is a flow regulator, typically constituted by an elastic clamp for gripping with adjustable intensity a flexible pipe that connects the sac to the drip chamber. As an alternative to the elastic clamp, for dosage of the liquid a precision regulator of a rotary type can be used, which is also in any case distinct and separate from the drip chamber.

SUMMARY OF THE INVENTION

The purpose of the present invention is to provide a drip chamber of the aforesaid type, configured in such a way as to reduce the number of loose components of the medical line, ensuring at the same time a greater convenience and practicality of regulation during use.

According to the invention, the above purpose is achieved thanks to the fact that the drip chamber is integrated with a precision flow regulator.

According to a preferred embodiment of the invention the flow regulator comprises a first body with an inlet fitting and a second body with an outlet fitting coupled together in a rotary way, with the interposition of a gasket, to open progressively the communication between said inlet fitting and said outlet fitting through dosage passages, and in which the second body bears a graduated scale co-operating with an indicator carried by the first body and has an annular attachment skirt permanently fixed on the inlet end of the body of the drip chamber.

BRIEF DESCRIPTION OF THE DRAWINGS

The invention will now be described in detail with reference to the annexed plate of drawings, which are provided purely by way of non-limiting example and in which.

DETAILED DESCRIPTION OF THE INVENTION

Figure 1:
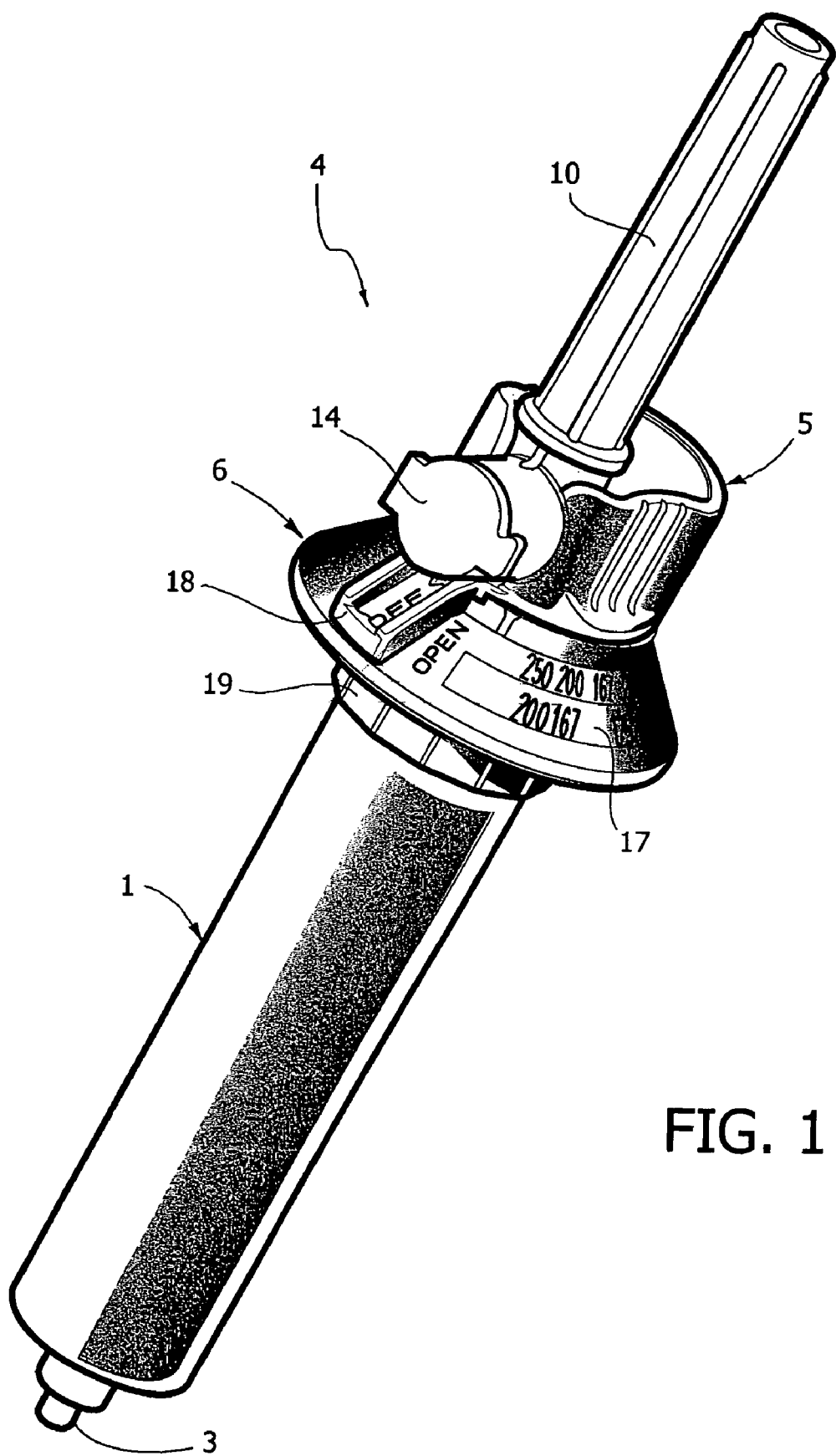
FIG. 1 is a schematic perspective view of a drip chamber with integrated flow regulator according to the invention.
Figure 2:
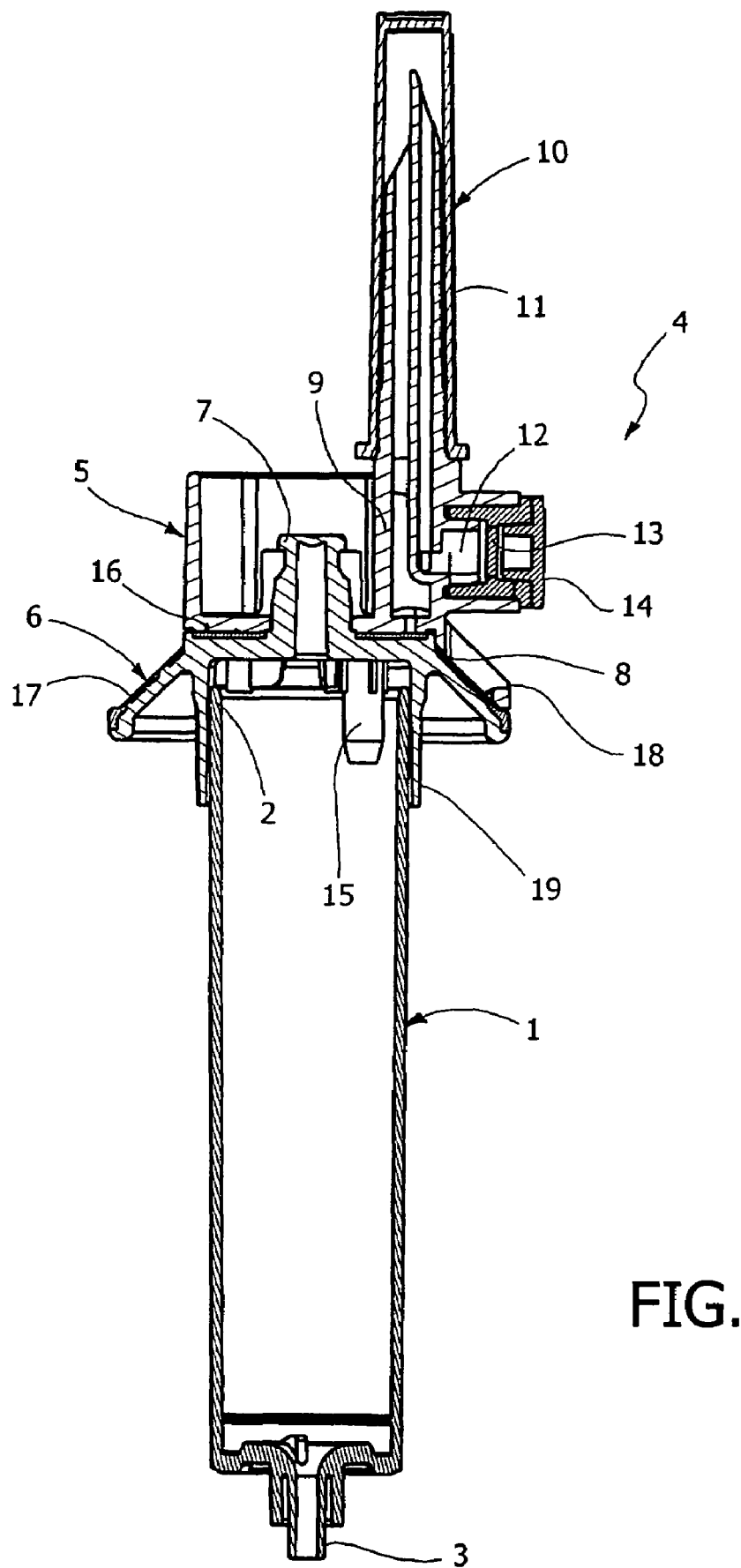
FIG. 2 is an axial cross-sectional view of FIG. 1.

With reference to FIGS. 1 and 2, a drip chamber according to the invention basically comprises a generally cylindrical body 1 made of transparent plastic material having one open end, which defines an inlet 2, and a restricted opposite end, which defines an outlet 3. According to the invention, directly applied on the inlet 2 is a precision flow regulator, designated as a whole by 4.

The flow regulator 4 comprises, in a generally known way, a first body 5 and a second body 6 both made of moulded plastic material and coupled together in a rotary way via a central pin 7, with the interposition of a gasket 8.

The first body 5 is formed integrally with an axial inlet fitting 9, the outer part of which is shaped like a perforating tip 10, applied on which is a removable protection cap 11. The inlet fitting 9 is moreover formed integrally with a side aeration passage 12 with associated filter 13 and openable closing plug 14.

The second body 6 is formed integrally with an outlet fitting 15, communication of which with the inlet fitting 9 is finely and progressively adjustable by means of relative rotation between the bodies 5 and 6, through dosage passages of said body 5, one of which is designated as a whole by 16 in FIG. 2. The modalities via which said progressive regulation is obtained are generally known, and for reasons of brevity will not be described in detail.

For controlling regulation, at least one graduated scale 17 (or a different indication representing a greater or smaller flow rate) is provided, formed peripherally on the body 6 and co-operating with a window indicator 18, formed integrally with the body 5. The graduated scale 17 can be conveniently made according to what is described and illustrated in the Italian patent application No. TO2005A00394, not published at the date of filing of the present application.

The body 6 is moreover formed integrally with an annular skirt 19, projecting from the part opposite to the body 5 and fixed permanently on the outside of the inlet 2 of the drip chamber 1, via gluing or with any suitable equivalent system. The outlet fitting 15, contained within the skirt 19, projects in this way within the body I of the drip chamber.

Figure 3:
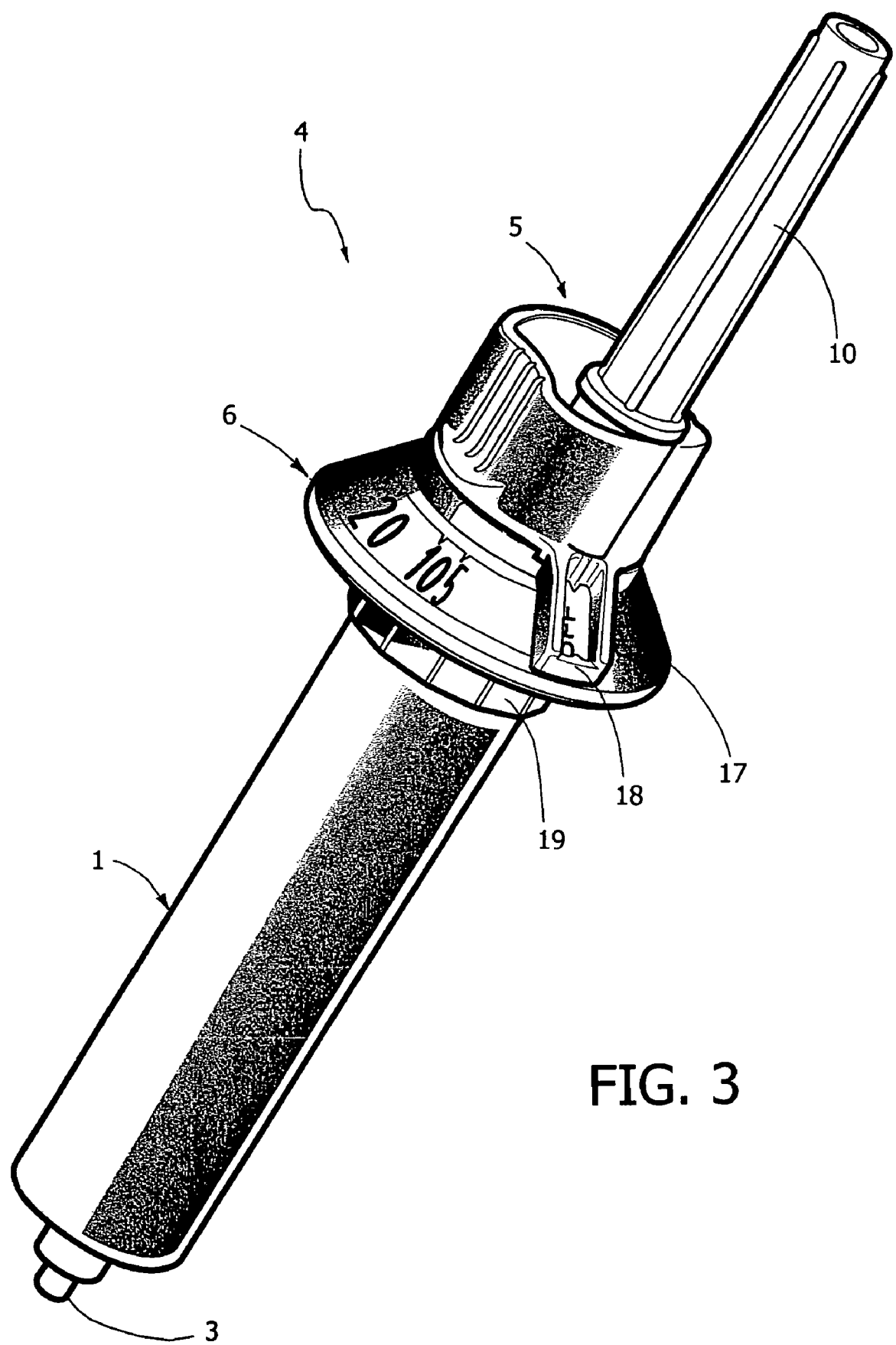
FIG. 3 shows a variant of FIG. 1.

The variant of FIG. 3, in which parts that are identical or similar to the ones already described with reference to FIGS. 1 and 2 are designated by the same reference numbers, differs from the preceding embodiment only as regards the absence of the side aeration passage and corresponding plug. This variant is usable in the case where the drip chamber is to be used for a sac for medical liquid, whilst the previous embodiment is designed for use with medical liquids contained in bottles.

Integration between the body 1 of the drip chamber and the precision regulator 4 advantageously enables, on the one hand, reduction and compacting of the number of the components necessary for the medical line to which the drip chamber is associated, and on the other renders appreciably more convenient and easy the operations of regulation of the flow through said line by the personnel responsible.

Of course the details of construction and the embodiments may vary widely with respect to what is described and illustrated herein, without thereby departing from the scope of the invention, as defined in the ensuing claims.

What is claimed is:

1. A drip chamber for medical lines, including:
    a generally cylindrical body having an inlet and an outlet and a precision flow regulator integrated therewith;
    said precision flow regulator comprising a first body having an inlet fitting and a second body having an outlet fitting, said first and second body being coupled together in a rotary way with the interposition of a gasket so as to open progressively the communication between said inlet fitting and said outlet fitting through dosage passages, said second body having an annular attachment skirt permanently fixed on said inlet end of the body of the drip chamber;
    said second body bearing a peripheral graduated scale co-operating with an indicator of said first body, said indicator consisting of an integral side appendage of said first body shaped as a window projecting from a side wall of said first body and over said graduated scale, so as to form a raised window framing at least one value of said peripheral graduated scale while leaving other values thereof visible.

2. The drip chamber according to claim 1, wherein said inlet fitting of the first body of said flow regulator is formed as a perforating tip.

3. The drip chamber according to claim 2, wherein said inlet fitting of the first body of said flow regulator further comprises an aeration passage with an associated filter and openable closing plug.

4. A drip chamber for medical lines, including:
a generally cylindrical body having an inlet and an outlet and a precision flow regulator integrated therewith;
said precision flow regulator comprising a first body having an inlet fitting and a second body having an outlet fitting, said first and second body being coupled together to allow rotation therebetween about an axis of said generally cylindrical body;
a gasket interposed between said first body and said second body and configured so as to open progressively a communication between said inlet fitting and said outlet fitting through dosage passages in response to a rotation of said first body and said second body relative to each other;
said inlet fitting and said outlet fitting located on opposite sides of said gasket axially relative to said axis of said generally cylindrical body, said inlet fitting and said outlet fitting having axes parallel and offset relative to each other;
said second body having on annular attachment skirt permanently fixed on an inlet end of the cylindrical body of the drip chamber, said outlet fitting extending into said inlet; and
said second body bearing a peripheral graduated scale cooperating with an indicator of said first body, said indicator consisting of an integral side appendage of said first body shaped as a window, said indicator projecting from a side wall of said first body and over said graduated scale of said second body, so as to form a raised window framing at least one value of said peripheral graduated scale inside said indicator, and wherein a remainder of said graduated scale is unframed by said indicator and uncovered to leave said graduated scale visible.

\* \* \* \* \*